US006685968B1

(12) United States Patent
West

(10) Patent No.: US 6,685,968 B1
(45) Date of Patent: Feb. 3, 2004

(54) BORIC ACID SAPSTAIN CONTROL METHOD

(76) Inventor: Michael Howard West, 54 S. Crockett Rd., Senatobia, MS (US) 38668

( * ) Notice: Subject to any disclaimer, the term of this patent is extended or adjusted under 35 U.S.C. 154(b) by 12 days.

(21) Appl. No.: 10/389,607

(22) Filed: Mar. 17, 2003

(51) Int. Cl.[7] ........................ A01N 59/14; A61K 33/22

(52) U.S. Cl. ...................................................... 424/659

(58) Field of Search ......................................... 424/659

(56) References Cited

U.S. PATENT DOCUMENTS 3,874,871 A * 4/1975 Sy et al. ........................ 71/68

FOREIGN PATENT DOCUMENTS

| | | |
|---|---|---|
| JP | 54143501 | * 11/1979 |
| SU | 1698062 | * 12/1991 |

* cited by examiner

*Primary Examiner*—Alton N. Pryor

(57) ABSTRACT

A method for protecting fresh cut lumber and logs from sapstain which comprises applying a 1–10% aqueous boric acid solution to the wood surface.

1 Claim, No Drawings

BORIC ACID SAPSTAIN CONTROL METHOD

CROSS REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

The field of endeavor to which this invention pertains relates to the fungicidal protection of fresh cut lumber and logs from sapstain by applying a 1–10% aqueous solution of boric acid to the wood surface. The problem solved is failure of boric acid salts to control sapstain, alone, or in combination with other fungicides currently available. Sodium borates have a history of sapstain control in combination with pentachlorophenates; but these toxic fungicides are no longer available. I have found that boric acid is an effective sapstain control fungicide when used alone; and, unlike boric acid salts, is compatible with other wood protection materials.

BRIEF SUMMARY OF THE INVENTION

The substance of the claimed invention relates to a method for protecting fresh cut lumber and logs from sapstain by applying a 1–10% aqueous boric acid solution to the wood surface. The substance of the invention includes the addition of other wood protection materials to the boric acid solution.

DETAILED DESCRIPTION OF THE INVENTION

Boric acid has limited solubility in water. Water to which more than 4% boric acid is added requires warming, or the addition of other wood protection material which also increase boric acid solubility. Powdered boric acid dissolves more quickly than the crystals, and it constitutes the preferred embodiment of my invention.

Aqueous solutions containing 1,3,5,7, and 10% boric acid according to my preferred embodiment were prepared and used to treat fresh cut hackberry lumber by dipping. Aqueous disodium octaborate tetrahydrate solutions containing the same level of boric oxide were prepared and used in the same manner. This treated lumber, and untreated controls, was stacked in accordance with standard sawmill air drying practice. After six months of seasoning the lumber was planed, and examined for sapstain control. The boric acid concentrations gave superior sapstain control compared to the DOT concentrations, which were in turn superior to the untreated controls.

I claim:

1. A method for protecting fresh cut lumber and logs from sapstain which consists essentially of applying a 1–10% aqueous boric acid solution to the surface of the cut lumber and logs.

* * * * *